United States Patent [19]

Simon

[11] 4,000,310

[45] Dec. 28, 1976

[54] PHARMACEUTICAL COMPOSITIONS CONTAINING 6-METHYL-3,4-DIPHENYL-3,4,5,6-TETRAHYDRO-2-PYRONE OR DERIVATIVES THEREOF

[75] Inventor: Pierre Simon, Sevres, France

[73] Assignee: Union Chimique Continentale-U.C.C, Puteaux, France

[22] Filed: July 1, 1975

[21] Appl. No.: 592,342

[30] Foreign Application Priority Data

July 10, 1974 France .............................. 74.23928

[52] U.S. Cl. .............................................. 424/279
[51] Int. Cl.$^2$ .................................... A61K 31/335

[58] Field of Search .................................. 424/279

[56] References Cited

OTHER PUBLICATIONS

Chem. Abst., vol. 72—110920u (1970).

*Primary Examiner*—Stanley J. Friedman
*Attorney, Agent, or Firm*—Browdy and Neimark

[57] ABSTRACT

6-Methyl-3,4-diphenyl-3,4,5,6-tetrahydro-2-pyrone or derivatives thereof are psychostimulants which can be administered orally, parenterally and rectally. An effective oral dose for an adult is 100–1000 mg/day.

12 Claims, No Drawings

PHARMACEUTICAL COMPOSITIONS CONTAINING 6-METHYL-3,4-DIPHENYL-3,4,5,6-TETRAHYDRO-2-PYRONE OR DERIVATIVES THEREOF

FIELD OF THE INVENTION

This invention relates to pharmaceutical compositions containing as the active constituent 6-methyl-3,4-diphenyl-3,4,5,6-tetrahydro-2-pyrone and its derivatives.

BACKGROUND OF THE INVENTION AND PRIOR ART 6-methyl-3,4-diphenyl-3,4,5,6-tetrahydro-2-pyrone, (MDTP), in its various isomeric forms, has been described in "A study of the Michael reaction. III — Outline of the products of addition of benzyl cyanide with 4-phenyl 3-butene 2-one trans", (A.M. Baradel, R. Longeray and J. Dreux, Bulletin de la Société Chimique de France, 1970, No. 1 p. 255–258.).

However, although 6-methyl-3,4-diphenyl-3,4,5,6-tetrahydro-2-pyrone is known as a chemical compound from the above mentioned publication, there has been no disclosure of any industrial application nor any therapeutic application for the same.

Applicants have made the surprising discovery that MDTP is pharmaceutically active and has psychotropic and psychostimulating properties.

Although many pharmaceuticals with a psychostimulating action are known, most of them in fact give rise to troublesome side effects when they are administered, such as motor incoordination, change in the diameter of the pupils, hyperthermia, etc.

OBJECTS OF THE INVENTION

An object of the invention is to provide a new medicament with psychostimulating properties, which will meet practical requirements better than known psychostimulating drugs. This is chiefly because its active constituent, 6-methyl-3,4-diphenyl-3,4,5,6-tetrahydro-2-pyrone, has a psychostimulating action which is different from that of known medicaments and gives rise to virtually no side effects. even in doses larger than the therapeutic quantity.

A further object of the invention a new medicament with valuable therapeutic, particularly psychostimulating, properties, comprising 6-methyl 3,4-diphenyl 3,4,5,6-tetrahydro 2-pyrone which is present in one or more of its isomeric forms, which complies with formula I below:

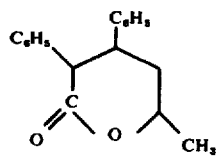

(I)

and which may be associated with appropriate pharmaceutical media to allow for its oral, parenteral or rectal administration.

A further object of the invention is a pharmaceutical composition comprising a carrier and a compound of formula (I) above in which one or more hydrogen atoms from the methyl and/or phenyl groups of the MDTP of formula I is substituted by a substituted or unsubstituted alkyl, cycloalkyl, aryl or aralkyl group or by an —SH, —OH, —NH$_2$ or NO$_2$ group.

Apart from the above embodiments the invention includes others which can be seen from the detailed description which follows.

The invention more particularly covers new medicaments containing MDTP in accordance with the above embodiments, and the various forms of administration in which they are prepared.

The invention will be better understood from the detailed description, which refers to an account of pharmacological and pharmacodynamic experiments demonstrating the effectiveness of the new medicaments according to the invention.

DETAILED DESCRIPTION OF THE INVENTION

All the experiments described below were carried out using male rats weighing from 170 to 220 g (Wistar Af stock) and male mice weighing from 18 to 23 g (Swiss NMRI stock).

All the experiments took place in a laboratory with a constant temperature (22° ± 1° C).

All the experiments were carried out blind (without the experimenter knowing, at the time of the tests, which animals had received the substance presumed active).

Unless otherwise stated, 10 animals were always used per point.

DETERMINATION OF ACUTE TOXICITY IN THE MOUSE

The LD$_{50}$ (determined by the method of Behrens and Karber) of 6-methyl 3,4-diphenyl 3,4,5,6-tetrahydro 2-pyrone (or MDTP), administered orally, was 625 mg/kg; with intraperitoneal administration the LD$_{50}$ was 150 mg/kg.

In the rat, with either oral or intraperitoneal administration, the LD$_{50}$ of 6-methyl 3,4-diphenyl-3,4,5,6-tetrahydro 2-pyrone was over 300 mg/kg.

OBSERVATION OF THE ANIMALS

In the rat as in the mouse, at doses below the toxic level (and from 16 mg/kg with oral or intraperitoneal administration), slight excitation is observed with increased reaction to touching or to sound stimuli. This stimulation is not accompanied by motor incoordination or by abnormal or stereotyped movements. Furthermore no change in diameter of the pupils or the rectal temperature is observed under these conditions.

It is only at doses very close to the lethal level that one can observe: tremors, hyperreactivity to very intense stimuli, interaggressiveness and convulsive phenomena with the rear paws stretched. Under these conditions moderate hyperthermia is also observed.

An increase in sexual behaviour is also observed in the rat.

MOTOR ACTIVITY IN THE MOUSE

Motor activity was determined using actimeters with photoelectric cells (Boissier and Simon, Arch. int. Pharmacodyn., 1965, 158, 212–221). A minimum of 12 animals were always used per point.

a. MDTP is administered orally at variable times before activity is measured. Under these conditions the increase in motor activity brought about by MDTP (64 mg/kg) is maximal if pretreatment is carried out 15 or 30 minutes before the actograph is taken (221 and 192% respectively relative to the control group). There is also a marked increase if pretreatment is effected 60 or 120 minutes before the actograph is taken (161 and 136% respectively relative to the control group).

b. When administered orally 30 minutes before the actograph is taken, MDTP increases the motor activity of mice. The increase becomes significant from a dose of 32 mg/kg and is proportional to the dose administered.

c. When administered orally immediately before the actograph is taken, MDTP (128 mg/kg) brings a marked increase in the motor activity of mice up to the 150th minute (Table I).

TABLE I

| | Number of bars passed over by mice: | | | | | |
|---|---|---|---|---|---|---|
| | 0 to 30 min | 30 to 60 min | 60 to 90 min | 90 to 120 min | 120 to 150 min | 150 to 180 min |
| Control group | 390 | 82 | 12 | 15 | 14 | 8 |
| MDTP (128 mg/kg orally) | 846 | 428 | 244 | 99 | 66 | 25 |

MOTOR ACTIVITY IN THE RAT

Motor activity was determined with the aid of actimeters with photoelectric cells described by Tedeschi and Coll (J. Pharm. sci. 1964, 53, 1046–1049). A minimum of 10 animals were always used per point. The results are set out in table II. They show a large increase in the motor activity of rats, which becomes significant from a dose of 32 mg/kg given orally.

TABLE II

| Number of bars passed over (as % of control group) after: | | | | | | |
|---|---|---|---|---|---|---|
| MDTP mg/kg given orally 15 min before test started | 5 min | 10 min | 15 min | 20 min | 25 min | 30 min |
| 16 | 131 | 135 | 148 | 145 | 144 | 133 |
| 32 | 186 | 184 | 135 | 138 | 155 | 161 |
| 64 | 155 | 181 | 178 | 200 | 186 | 195 |
| 128 | 210 | 215 | 209 | 217 | 215 | 201 |

TEST WITH THE BOARD CONTAINING HOLES

The method and apparatus described by BOISSIER and SIMON (Physiol. Behav. 1967, 2, 444–448) were used. During these experiments 15 animals were used per batch (except that 30 were used for the control group and 30 for the dose of 64 mg/kg). The results set out in Table III show a marked increase in displacements, confirming the increase in motility which was observed in actography and also a large increase in the number of holes explored, which becomes significant from a dose of 32 mg/kg.

TABLE III

| MDTP mg/kg given orally 60 min before test | % of control group holes explored in 5 min | displacements made in 5 min |
|---|---|---|
| 16 | 120 | 98 |
| 32 | 131 | 115 |
| 64 | 140 | 161 |
| 128 | 141 | 159 |

HOT-PLATE TEST ON THE MOUSE

This test was applied to measure the time taken or animals to react to a painful stimulus. 12 animals were used per point. 15 Minutes after oral administration of MDTP (64 mg/kg) the time taken for mice exposed to the hot-plate to react (by licking their rear paws) was 5.9 seconds, whereas the time taken by the control group was 9.5 seconds (difference significant at the threshold of 0.01).

On the other hand, the effects on this test of an analgesic dose of morphine was not changed — either by increasing or reducing them — by MDTP at the same dose.

Other tests were applied and showed no effects of MDTP. The tests are important in that they enable the effectiveness of the substance to be outlined and compared with that of other known psychotropic substances. They are also important in demonstrating the absence of any change in a certain number of normal forms of behaviour.

a. No disturbance of an avoidance conditioning

The avoidance conditioning was studied in the rat placed in a shuttle-box (with 2 compartments) (of. BOISSIER and SIMON: Therapie 1968, 23, 1267–1276). In rats which had previously been trained and which made over 90% of conditioned responses MDTP, given orally in a dose of 64 mg/kg, did not produce any change in conditioning (8 animals were studied).

b. No disturbance of an inhibiting conditioning

A simple conditioned inhibition test was used, the 4 plate test (ARON an Coll, Neuropharmacology 1971, 10, 459–470). In doses of 4, 8, 16, 32, 64 and 128 mg/kg (10 animals per batch) no change was observed in conditioned inhibition in the mouse. During this test a slight increase in the performance of the animals was indeed observed, although this appears to be connected with the stimulating action mentioned previously.

c. No change in effects of hypnotics

Oral administration of MDTP in doses of 16, 32 or 64 mg/kg, simultaneously with or 60 minutes before the administration of barbiturate hypnotics (pentabarbitone or barbitone sodium) did not produce any change in the time taken to fall asleep or in the sleeping period in either the mouse or the rat.

d. No effects on conventional antidepressant tests

1. Test for antireserpine action:
When administered orally in doses of 8, 16, 32 and 64 mg/kg to mice and rats pretreated with reserpine (2.5 mg/kg given intraperitoneally 4 hours before the MDTP), MDTP did not produce any change in the hypothermia or palpebral ptosis induced by the reserpine.

2. Test for antioxotremorine action
In mice which had been dosed intraperitoneally or orally with 8, 16, 32 or 64 mg/kg of MDTP, the effects of oxotremorine (0.5 mg/kg given intraperitoneally) were unchanged, as far as hypothermia, tremors, tears, hypersalivation and defecation were concerned.

3. Test of anticataleptic action

In rats which had been made cataleptic by intraperitoneal administration of 8 mg/kg of prochlorperazine, intraperitoneal or oral administration or MDTP (16 or 64 mg/kg) did not produce any change in the cataleptic state, as assessed either by the crossing of homolateral paws test, the Buddha test or the elevator test.

4. Amphetamine stereotypy test

Oral administration of MDTP (32, 64 or 128 mg/kg) 60 minutes before an intraperitoneal dose of 2 mg/kg of amphetamine did not bring about any change in the stereotyped movements induced in the rat by the amphetamine.

5. Apomorphine stereotypy test

Oral administration of MDTP (32, 64 or 128 mg/kg) 60 minutes before a subcutaneous injection of 0.5 mg/kg of apomorphine did not bring about any change in the sterotyped movements induced in the rat by the apomorphine.

e. No inhibiting effect on monoamine oxidase

It was confirmed that MDTP did not increase the effects of tryptamine on the rat when given intraperitoneally in a dose of 64 mg/kg. The dose of tryptamine given was insufficient to induce convulsions (3 mg/kg by intravenous injection).

f. No interaction with convulsion-inducing agents

In connection with electric shocks applied to the mouse MDTP administered orally in doses of 16, 32, 64 or 128 mg/kg 60 minutes before the shock, did not affect either the duration or the form of the convulsive attacks and did not lead to any increase in mortality after the attack.

When administered orally in a dose of 64 mg/kg 30 minutes before a convulsion-inducing dose of cardiazol (160 mg/kg by subcutaneous injection), MDTP did not reduce the latency of the convulsion-inducing attacks.

On the basis of the above findings the effects of MDTP can be summarised as follows:

an increase in the activity and alertness of animals without abnormal behavour and particularly stereotyped movements ever appearing. Increased activity and alertness were found in both the rat and the mouse by observing the animals, measuring their motor activity and measuring their exploration of a board containing holes and the shortening of the reaction time of mice on a hot-plate. The increase is marked (according to the tests) from doses of 16 to 32 mg/kg given orally; it takes place rapidly after administration and lasts about 2 hours. These doses are far from the toxic level (ratio LD50/ED 50 approximately 20/1 in the mouse and over 10/1 in the rat);

the increase in activity and alertness is not accompanied by any disturbance of conditioned behaviour;

in really stimulating doses MDTP does not counteract the effects of hypnotics;

it has no effects on the usual tests for tricyclic antidepressants;

it has no inhibiting effect on monoamine oxidase (tryptamine test).

This outline makes it possible to class MDTP among the psychoanaleptics (by the internationally accepted classification of Jean DELAY and Pierre DENIKER). Within the group of psychoanaleptics MDTP can be clearly distinguished from the following categories;

nooanaleptics (or amphetamines); unlike these substances MDTP does not give rise to any signs of sympathetic excitation, any sleep preventing action, any stereotyped movements or any antireserpine or anticataleptic action;

thymoanaleptics (or tricyclic antidepressants); unlike these substances MDTP has a stimulating action on normal animals but has no effect on tests for antireserpine, antioxotremorine or anticataleptic action;

thymeretics (or inhibitors of monoamine oxidase); unlike these substances MDTP has no effect on tests for antireserpine and anticataleptic action and does not enhance amphetamine stereotypy. Furthermore MDTP does not enhance the effects of tryptamine on the rat.

From the effects observed it can be concluded that MDTP is a psychostimulant with an action similar to that of caffeine. However there is a fundamental difference between MDTP and caffeine; MDTP does not have any sleep inhibiting effect, whereas caffeine does.

On the basis of the pharmacological and pharmacodynamic properties just mentioned, MDTP should be considered as a novel psychostimulant adapted to exert a stimulating action on the human being, with an increase in alertness. It can therefore be applied therapeutically to the following indications:

in children: difficulties in intellectual concentration, listlessness, asthenia, restlessness, troubles in memorising and difficulty in being attentive;

in adults and the elderly; asthenia, decrease in intellectual activity, listlessness, correction of states of sedation brought on by administering antipeleptics, tranquillisers, neuroleptics or other medicaments, listlessness from Parkinson's disease;

effects of stimulation on patients suffering from depressive states or a reduction of sexuality (libido).

The new medicaments according to the invention may be administered orally in the form of compressed tablets, sugar coated pills, soft gelatine capsules (gelules), capsules, microcapsules, etc., or in liquid form, or may be given rectally in association with appropriate media or parenterally in the form of injectable solutions. Effective doses for oral administration are from 100 to 1,000 mg/day for adults.

However they are administered, the new medicaments according to the invention accordingly have many advantages over known psychostimulants, the main advantage being their increased stimulating action and the virtually total absence of any side effects.

We claim:

1. A pharmaceutical composition for producing a psychostimulant effect comprising 6-methyl-3,4-diphenyl-3,4,5,6-tetrahydro-2-pyrone present in one or more of its isomeric forms, according to formula I:

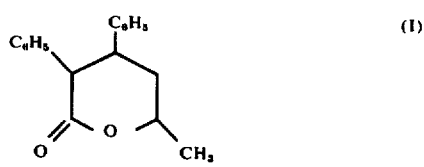

in a psychostimulant-effective amount, and a pharmaceutical diluent.

2. Pharmaceutical composition according to claim 1, comprising a compound according to formula I in which one or more hydrogen atoms from the methyl or phenyl groups of said compound of formula I are substituted by substituted and unsubstituted alkyl, cycloalkyl, aryl and aralkyl groups or by —SH, —OH, —NH$_2$, —NO and —NO$_2$ groups.

3. A pharmaceutical composition for producing a psychostimulant effect, in unit dosage form comprising a pharmaceutical diluent and 1 mg to 10 mg of 6-methyl-3,4-diphenyl-3,4,5,6-tetrahydro-2-pyrone.

4. A method of producing a psychostimulant effect in a patient in need of said therapy comprising
   administering to a patient in need of such therapy a stimulant- effective, non-toxic amount of 6-methyl-3,4-diphenyl-3,4,5,6-tetrahydro-2-pyrone.

5. The method of claim 4, wherein the compound is orally administered to an adult patient in amounts of 100 to 1000 mg per day.

6. A method in accordance with claim 4 for increasing motor activity.

7. A method in accordance with claim 4 for reducing the time to which a patient will react to a stimulus.

8. A method in accordance with claim 4 for increasing the activity and alertness of said patient.

9. A method in accordance with claim 4, wherein said patient is a child, and for improving intellectual concentration and for reducing listlessness, asthenia, restlessness, troubles in memorizing and difficulty in being attentive.

10. A method in accordance with claim 4, wherein the compounded is administered to an adult patient, and for reducing asthenia, restlessness, troubles in memorizing and difficulty in being attentive.

11. A method in accordance with claim 4, wherein the compound is administered to an adult patient, and for reducing asthenia and listlessness and for increasing intellectual activity, and for correcting states of sedation brought on by administering antiepileptics, tranquilizers, neuroleptics.

12. A method in accordance with claim 4 for stimulating said patient suffering from depression.

* * * * *